United States Patent
Krause et al.

(10) Patent No.: US 6,835,695 B2
(45) Date of Patent: Dec. 28, 2004

(54) HERBICIDAL COMPOSITIONS

(75) Inventors: Hans-Peter Krause, Hofheim (DE); Jean Kocur, Hofheim (DE); Julio Martinez de Una, Liederbach (DE); Udo Bickers, Wietmarschen (DE); Erwin Hacker, Hochheim (DE); Gerhard Schnabel, Elsenfeld (DE)

(73) Assignee: Aventis CropScience GmbH, Frankfurt am Main (DE)

( * ) Notice: Subject to any disclaimer, the term of this patent is extended or adjusted under 35 U.S.C. 154(b) by 76 days.

(21) Appl. No.: 09/882,395

(22) Filed: Jun. 15, 2001

(65) Prior Publication Data

US 2002/0137634 A1 Sep. 26, 2002

(30) Foreign Application Priority Data

Jun. 19, 2000 (DE) .......................................... 100 29 165

(51) Int. Cl.$^7$ ............................................. A01N 35/00
(52) U.S. Cl. ....................................................... 504/348
(58) Field of Search ......................................... 504/348

(56) References Cited

U.S. PATENT DOCUMENTS

| | | | | |
|---|---|---|---|---|
| 4,762,551 | A | * 8/1988 | Knudsen | ...................... 71/103 |
| 5,650,533 | A | * 7/1997 | Roberts et al. | ................ 560/17 |
| 6,133,217 | A | * 10/2000 | Lewis et al. | ................. 510/351 |
| 6,451,731 | B1 | * 9/2002 | Agbaje et al. | ............... 504/118 |

FOREIGN PATENT DOCUMENTS

| | | |
|---|---|---|
| AU | 4370399 | 12/1999 |
| AU | 4102800 | 9/2000 |
| EP | 0 968 649 | 1/2000 |
| WO | WO 92/19107 | 11/1992 |
| WO | WO 98/31223 | 7/1998 |
| WO | WO 98/42678 | 10/1998 |
| WO | WO 99/23886 | 5/1999 |
| WO | WO 99/63823 | 12/1999 |
| WO | WO 00/30477 | 6/2000 |
| WO | WO 00/53014 | 9/2000 |

OTHER PUBLICATIONS

Young et al, "Optimizing Foliar Activity of Isoxaflutole on Giant Foxtail (*Setaria faberi*) with Various Adjuvants", Weed Science, 46:397–402, 1998.

* cited by examiner

*Primary Examiner*—Alton Pryor
(74) *Attorney, Agent, or Firm*—Frommer Lawrence & Haug LLP

(57) ABSTRACT

The present invention relates to a herbicidal composition comprising

A) one or more compounds of the formula (I)

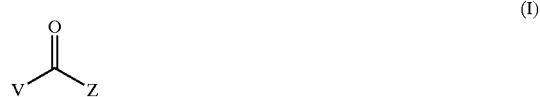

(I)

where V is an unsubstituted or substituted heterocyclyl radical or a radical —$CR^\alpha$=$CR^\beta R^{\beta 1}$, where $R^\alpha$ and $R^\beta$ are identical or different carbon-containing $C_1$–$C_{40}$ radicals which together can form an unsubstituted or substituted ring, and $R^{\beta 1}$ is OH or a carbon-containing $C_1$–$C_{40}$ radical, and Z is an unsubstituted or substituted aryl radical, and B) one or more surfactants comprising, as structural element, at least 10, alkylene oxide units.

1 Claim, No Drawings

HERBICIDAL COMPOSITIONS

The invention is in the technical field of the crop protection products, in particular, the invention relates to herbicidal compositions with a content of particular herbicidal compounds and specific surfactants which are outstandingly suitable for controlling harmful plants in crops.

Some of the more recent herbicidal active ingredients which inhibit p-hydroxyphenyl-pyruvate dioxygenase (HPPDO) show very good properties on use and can be employed in very low rates of application against a broad spectrum of graminaceous and broad-leaved weeds (see, for example, Prisbylla et al., Brighton Crop Protection Conference—Weeds (1993), 731–738).

U.S. Pat. No. 5,627,131 and EP 551650 disclose specific mixtures of herbicides with pre-emergence safeners.

It is furthermore known from various publications that herbicides from the series of the benzoylcyclohexanediones, being inhibitors of para-hydroxyphenyl-pyruvate dioxygenase, are based on the same mechanism of action as those from the series of the benzoylisoxazoles; in this context cf. J. Pesticide Sci. 21, 473–478 (1996); Weed Science 45, 601–609 (1997), Pesticide Science 50, 83–84, (1997) and Pesticide Outlook, 29–32, (December 1996). Moreover, it is known from Pesticide Science 50, 83–84, (1997) that, under certain conditions, benzoylisoxazoles can undergo rearrangements to give benzoyl-3-oxopropionitriles.

It is likewise known that the abovementioned herbicidal compounds can be combined with surfactants to produce standard formulations.

Thus, for example, WO 98/31223 describes the use of mixtures comprising a fatty acid ester or an alkoxy fatty acid, a terpene derivative and a pesticide. EP-A 0 968 649 describes dry formulations of herbicides comprising ethoxylated fatty alcohols. The herbicide-comprising mixtures mentioned therein do not always exhibit the desired potent herbicidal action.

The object of the present invention was to provide herbicidal compositions which have a particularly potent herbicidal action.

Surprisingly, it has now been found that herbicidal compositions comprising the compounds of the formula (I) stated hereinbelow in combination with specific surfactants achieve this object.

Thus, the present invention relates to herbicidal compositions comprising

A) one or more compounds of the formula (I)

(I)

where V is an unsubstituted or substituted heterocyclyl radical or a radical —$CR^\alpha$=$CR^\beta$ $R^{\beta 1}$, where $R^\alpha$ and $R^\beta$ are identical or different carbon-containing $C_1$–$C_{40}$ radicals which together can form an unsubstituted or substituted ring, and $R^{\beta 1}$ is OH or a carbon-containing $C_1$–$C_{40}$ radical, and Z is an unsubstituted or substituted aryl radical, and B) one or more surfactants comprising, as structural element, at least 10, preferably 10–200, alkylene oxide units.

Surfactant B) preferably contains 10–150 alkylene oxide units, one or more carbon-containing $C_1$–$C_{40}$ radicals and, if appropriate, one or more polar functional groups.

The term alkylene oxide units is preferably understood as meaning units of $C_2$–$C_{10}$-alkylene oxides, such as ethylene oxide, propylene oxide, butylene oxide or hexylene oxide, it being possible for the units within the surfactant to be identical or different from each other.

Suitable polar functional groups include anionic groups such as carboxylate, carbonate, sulfate, sulfonate, phosphate or phosphonate, cationic groups such as groups with a cationic nitrogen atom, for example a pyridinium group or an —$NR^y{}_3$-group, where $R^y$ radicals are identical or different and are H or an unsubstituted or substituted $C_1$–$C_{10}$-hydrocarbon radical such as $C_1$–$C_{10}$-alkyl, electrically neutral, polar groups such as carbonyl, imine, cyano or sulfonyl, or betainic groups such as

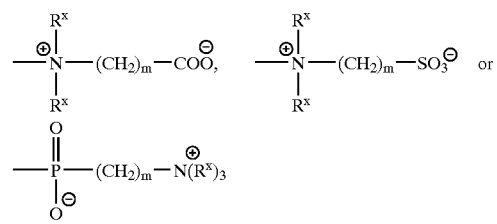

where m=1, 2, 3, 4 or 5 and $R^x$ are identical or different and are unsubstituted or substituted $C_1$–$C_{10}$-hydrocarbon radicals such as $C_1$–$C_{10}$-alkyl.

Preferably, the composition according to the invention comprises, as component B), one or more surfactants of the general formula (II)

$$R^\gamma\text{-}(EO)_x(PO)_y(EO)_z\text{—}R^\delta \qquad (II)$$

where
EO denotes an ethylene oxide unit,
PO denotes a propylene oxide unit,
x denotes an integer from 1 to 50,
y denotes an integer from 0 to 50,
z denotes an integer from 0 to 50,
where the total (x+y+z)≦10 and ≧150, and $R^\gamma$ denotes OH, an unsubstituted or substituted $C_1$–$C_{40}$-hydrocarbonoxy radical, an O-acyl radical such as O—$COR^1$, O—CO—$OR^1$, O—CO—$NR'R''$, O—P(O)($R'$)[(EO)$_u$($OR''$)] or O—P(O)[(EO)$_u$($OR'$)][(EO)$_u$($OR'$)] or $NR'R''$ or [$NR'R''R'''$]⁺$X^\ominus$, where $R'$, $R''$, and $R'''$ are identical or different and denote H or an unsubstituted or substituted $C_1$–$C_{30}$-hydrocarbon radical which can optionally be bound via a group (EO)$_w$, where w is an integer from 1 to 50, $X^\ominus$ is an anion (for example the anion of an organic acid such as a carboxylic acid anion, for example acetate or lactate, or the anion of an inorganic acid such as ½ sulfate, [O—$SO_3$—$CH_3$]$^\ominus$, sulfonate, ⅓ phosphate, phosphonate or halide such as $Cl^\ominus$ or $Br^\ominus$), and u, v independently of one another denote an integer from 0 to 50, and $R^\delta$ denotes H, an unsubstituted or substituted $C_1$–$C_{40}$-hydrocarbon radical, an acyl radical such as $COR^I$, CO—$OR^I$, CO—$NR'R''$, P(O)($R'$)[(EO)$_u$($OR''$)] or P(O)[(EO)$_u$($OR'$)][(EO)$_v$($OR''$)] or $NR'R''$ or [$NR'R''R'''$]⁺$X^\ominus$, where $R'$, $R''$ and $R'''$ are identical or different and denote H or an unsubstituted or substituted $C_1$–$C_{30}$-hydrocarbon radical which can optionally be bound via a group (EO)$_w$, where w is an integer from 1 to 50, $X^\ominus$ is an anion (for example the anion of an organic acid such as a carboxylic acid anion, for example acetate or lactate, or the anion of an inorganic acid such as ½ sulfate, [O—$SO_3$—$CH_3$]$^\ominus$, sulfonate, ⅓ phosphate, phosphonate or halide such as $Cl^\ominus$ or $Br^\ominus$), and u, v independently of one another denote an integer from 0 to 50.

The abbreviation EO in formula (II) denotes an ethylene oxide unit, also when used in the definition of $R^\gamma$ and $R^\delta$.

Preferred surfactants of the formula (II) are those where the total $(x+y+z) \geq 10$ and $\leq 150$, preferably 11–100, especially preferably 12–80, and $R^\gamma$ denotes OH, an unsubstituted or substituted $C_1$–$C_{30}$-hydrocarbonoxy radical, preferably a $C_4$–$C_{20}$-hydrocarbonoxy radical, such as a $C_8$-, $C_{10}$-, $C_{12}$-, $C_{13}$-(for example isotridecyl),$C_{14}$-,$C_{16}$-, $C_{18}$-, $C_{20}$-alkoxy radical, -alkenyloxy radical or -alkynyloxy radical, or an unsubstituted or substituted $C_6$–$C_{14}$-aryloxy radical, for example a $C_6$–$C_{14}$-aryloxy radical which is monosubstituted or polysubstituted by $C_1$–$C_{20}$-alkyl, such as p-octylphenoxy, p-nonylphenoxy, 2,4-dibutylphenoxy, 2,4,6-tri-isobutylphenoxy, 2,4,6-tri-n-butylphenoxy or 2,4,6-tri-sec-butylphenoxy, or $R^\gamma$ denotes O—CO—$R^I$, O—COO$R^I$, N$R^I R^{II}$ or [N$R^I R^{II} R^{III}$]$^\oplus X^\ominus$, where $R^I$, $R^{II}$ and $R^{III}$ are identical or different or denote H, an unsubstituted or substituted $C_1$–$C_{30}$-hydrocarbon radical, preferably a $C_4$–$C_{20}$-hydrocarbon radical, such as a $C_8$-, $C_{10}$-, $C_{12}$-, $C_{13}$-(for example isotridecyl), $C_{14}$-, $C_{16}$-, $C_{18}$-, $C_{20}$-alkyl radical, -alkenyl radical or -alkynyl radical, or an unsubstituted or substituted $C_6$–$C_{14}$-aryl radical, for example a $C_6$–$C_{14}$-aryl radical which is mono- or polysubstituted by $C_1$–$C_{20}$-alkyl such as p-octylphenyl, p-nonylphenyl, 2,4-dibutylphenyl, 2,4,6-tri-isobutylphenyl, 2,4,6-tri-n-butylphenyl or 2,4,6-tri-sec-butylphenyl, or $R^I$, $R^{II}$ and $R^{III}$ are identical or different and are (EO)$_w$—$R^{IV}$, where $R^{IV}$ is H or an unsubstituted or substituted $C_1$–$C_{20}$-hydrocarbon radical, such as a $C_8$-, $C_{10}$-, $C_{12}$-, $C_{13}$-(for example isotridecyl), $C_{14}$-, $C_{16}$-, $C_{18}$-, $C_{20}$-alkyl radical, -alkenyl radical or -alkynyl radical, or a $C_6$–$C_{14}$-aryl radical which is mono- or polysubstituted by $C_1$–$C_{20}$-alkyl such as p-octylphenyl, p-nonylphenyl, 2,4-dibutylphenyl, 2,4,6-tri-isobutylphenyl, 2,4,6-tri-n-butylphenyl or 2,4,6-tri-sec-butylphenyl and w is an integer from 1 to 50, and $X^\ominus$ is an anion, and $R^\delta$ denotes H, an unsubstituted or substituted $C_1$–$C_{30}$-hydrocarbon radical, preferably a $C_1$–$C_{20}$-hydrocarbon radical, such as a $C_1$-, $C_2$-, $C_3$-, $C_4$-, $C_5$-, $C_6$-, $C_8$-, $C_{10}$-, $C_{12}$-, $C_{13}$-(for example isotridecyl), $C_{14}$-, $C_{16}$-, $C_{18}$-, $C_{20}$-alkyl radical, -alkenyl radical or -alkynyl radical, or an unsubstituted or substituted $C_6$–$C_{14}$-aryl radical, for example a $C_6$–$C_{14}$-aryl radical which is mono- or polysubstituted by $C_1$–$C_{20}$-alkyl, such as p-octylphenyl, p-nonylphenyl, 2,4-dibutylphenyl, 2,4,6-tri-isobutylphenyl, 2,4,6-tri-n-butylphenyl or 2,4,6-tri-sec-butylphenyl, or $R^\delta$ denotes CO—$R^I$, COO$R^I$, N$R^I R^{II}$ or [N$R^I R^{II} R^{III}$]$^\oplus X^\ominus$, where $R^I$, $R^{II}$ and $R^{III}$ are identical or different and denote H, an unsubstituted or substituted $C_1$–$C_{30}$-hydrocarbon radical, preferably a $C_1$–$C_{20}$-hydrocarbon radical, such as a $C_1$-, $C_2$-, $C_3$-, $C_4$-, $C_5$-, $C_6$-,$C_8$-, $C_{10}$-, $C_{12}$-, $C_{13}$-(for example isotridecyl), $C_{14}$-, $C_{16}$-, $C_{18}$-, $C_{20}$-alkyl radical, -alkenyl radical or -alkynyl radical, or an unsubstituted or substituted $C_6$–$C_{14}$-aryl radical, for example a $C_6$–$C_{14}$-aryl radical which is mono- or polysubstituted by $C_1$–$C_{20}$-alkyl, such as p-octylphenyl, p-nonylphenyl, 2,4-dibutylphenyl, 2,4,6-tri-isobutylphenyl, 2,4,6-tri-n-butylphenyl or 2,4,6-tri-sec-butylphenyl, or $R^I$, $R^{II}$ and $R^{III}$ are identical or different and are (EO)$_w$—$R^{IV}$, where $R^{IV}$ is H or an unsubstituted or substituted $C_1$–$C_{30}$-hydrocarbon radical, preferably a $C_1$–$C_{20}$-hydrocarbon radical, such as a $C_1$-, $C_2$-, $C_3$-, $C_4$-, $C_5$-, $C_6$-, $C_8$-, $C_{10}$-, $C_{12}$-, $C_{13}$-(for example isotridecyl), $C_{14}$-, $C_{16}$-, $C_{18}$-, $C_{20}$-alkyl radical, -alkenyl radical or -alkynyl radical, or a $C_6$–$C_{14}$-aryl radical which is unsubstituted or substituted, for example mono- or polysubstituted by $C_1$–$C_{20}$-alkyl, such as p-octylphenyl, p-nonylphenyl, 2,4-dibutylphenyl, 2,4,6-tri-isobutylphenyl, 2,4,6-tri-n-butylphenyl or 2,4,6-tri-sec-butylphenyl and w is an integer from 1 to 50, and $X^\ominus$ is an anion.

Especially preferred surfactants of the formula (II) are those where the total $(x+y+z)$ equals 11–80, preferably 12–50, $R^\gamma$ is $(C_8$–$C_{18})$-alkoxy, $(C_8$–$C_{18})$-alkenyloxy or $(C_8$–$C_{18})$-alkynyloxy, $(C_7$–$C_{17})$-alkylcarbonyloxy, $(C_7$–$C_{17})$-alkenylcarbonyloxy, $(C_7$–$C_{17})$-alkynylcarbonyloxy, or $(C_1$–$C_{10})$-alkylphenoxy such as octylphenoxy, p-nonylphenoxy, 2,4,6-tri-n-butylphenoxy, 2,4,6-triisobutylphenoxy or 2,4,6-tri-sec-butylphenoxy, and $R^\delta$ is H, $(C_1$–$C_{18})$-, preferably $(C_1$–$C_6)$-alkyl, $(C_2$–$C_{18})$-, preferably $(C_2$–$C_6)$-alkynyl or $(C_2$–$C_{18})$-, preferably $(C_2$–$C_6)$-alkynyl, CO—H, CO—$(C_1$–$C_{17})$-alkyl, CO—$(C_2$–$C_{17})$-alkenyl or CO—$(C_2$–$C_{17})$-alkynyl.

Surfactants B), for example those of the formula (II), are known from the literature, for example from McCutcheon's, Emulsifiers & Detergents 1994, Vol. 1: North American Edition and Vol. 2, International Edition; McCutcheon Division, Glen Rock N.J., USA and from "Surfactants in Consumer Products", J. Falbe, Springer-Verlag Berlin, 1987. The surfactans B) stated herein are incorporated into this description by reference. Moreover, surfactants B), for example those of the formula (II), are also commercially available, for example under the trade names Genapol® X or O or T series, Sapogenat® T series, Arkopal® N series, Afilan® PTU, Hordaphos® and Emulsogen® series by Clariant AG; Agrilan® types by Akcros Organics; Alkamul® and Antarox® types by Rhodia; Emulan® types (NP, OC, OG, OK) by BASF AG; Dehydol® types by Henkel; Agent W® types by Stepan Company; Crodamel® types by Croda GmbH. The surfactants B) mentioned in the product leaflets in question are incorporated into this description by reference.

Examples of surfactants B), for example those of the formula (II) are stated in Table 1 hereinbelow:

TABLE 1

| Ex. No. | $R^\gamma$ | x | y | z | $R^\delta$ |
|---|---|---|---|---|---|
| 1 | octyl—O— | 10 | — | — | H |
| 2 | " | 12 | — | — | H |
| 3 | " | 15 | — | — | H |
| 4 | decyl—O— | 10 | — | — | H |
| 5 | " | 15 | — | — | H |
| 6 | " | 20 | — | — | H |
| 7 | tridecyl—O— | 10 | — | — | H |
| 8 | " | 11 | — | — | H |
| 9 | " | 12 | — | — | H |
| 10 | " | 13 | — | — | H |
| 11 | " | 14 | — | — | H |
| 12 | " | 15 | — | — | H |
| 13 | " | 16 | — | — | H |
| 14 | " | 17 | — | — | H |
| 15 | " | 18 | — | — | H |
| 16 | " | 19 | — | — | H |
| 17 | " | 20 | — | — | H |
| 18 | " | 25 | — | — | H |
| 19 | " | 30 | — | — | H |
| 20 | " | 15 | — | — | Me |

TABLE 1-continued

| Ex. No. | R^γ | x | y | z | R^δ |
|---|---|---|---|---|---|
| 21 | " | 17 | — | — | Me |
| 22 | " | 15 | — | — | COCH₃ |
| 23 | " | 17 | — | — | COCH₃ |
| 24 | (C₁₂—alkyl)—O— | 10 | — | — | H |
| 25 | " | 11 | — | — | H |
| 26 | " | 12 | — | — | H |
| 27 | " | 13 | — | — | H |
| 28 | " | 14 | — | — | H |
| 29 | " | 15 | — | — | H |
| 30 | " | 16 | — | — | H |
| 31 | (C₁₂—alkyl)—O— | 17 | — | — | H |
| 32 | " | 20 | — | — | H |
| 33 | " | 15 | — | — | Me |
| 34 | " | 15 | — | — | COCH₃ |
| 35 | (C₁₄—alkyl)—O— | 10 | — | — | H |
| 36 | " | 11 | — | — | H |
| 37 | " | 12 | — | — | H |
| 38 | " | 13 | — | — | H |
| 39 | " | 14 | — | — | H |
| 40 | " | 15 | — | — | H |
| 41 | " | 16 | — | — | H |
| 42 | " | 17 | — | — | H |
| 43 | " | 18 | — | — | H |
| 44 | " | 19 | — | — | H |
| 45 | " | 20 | — | — | H |
| 46 | " | 25 | — | — | H |
| 47 | " | 30 | — | — | H |
| 48 | " | 40 | — | — | H |
| 49 | (C₁₆—alkyl)—O— | 10 | — | — | H |
| 50 | " | 15 | — | — | H |
| 51 | " | 20 | — | — | H |
| 52 | " | 40 | — | — | H |
| 53 | (C₁₈—alkyl)—O— | 15 | — | — | H |
| 54 | " | 20 | — | — | H |
| 55 | (C₉—alkyl)—CO—O— | 10 | — | — | Me |
| 56 | " | 11 | — | — | Me |
| 57 | " | 12 | — | — | Me |
| 58 | " | 13 | — | — | Me |
| 59 | " | 14 | — | — | Me |
| 60 | " | 15 | — | — | Me |
| 61 | " | 16 | — | — | Me |
| 62 | " | 20 | — | — | Me |
| 63 | (C₁₀—alkyl)—CO—O— | 10 | — | — | Me |
| 64 | (C₁₀—alkyl)—CO—O— | 15 | — | — | Me |
| 65 | " | 20 | — | — | Me |
| 66 | (C₁₁—alkyl)—CO—O— | 10 | — | — | Me |
| 67 | " | 11 | — | — | Me |
| 68 | " | 12 | — | — | Me |
| 69 | " | 13 | — | — | Me |
| 70 | " | 14 | — | — | Me |
| 71 | " | 15 | — | — | Me |
| 72 | " | 16 | — | — | Me |
| 73 | " | 17 | — | — | Me |
| 74 | " | 20 | — | — | Me |
| 75 | " | 25 | — | — | Me |
| 76 | (C₁₂—alkyl)—CO—O— | 10 | — | — | Me |
| 77 | " | 15 | — | — | Me |
| 78 | " | 20 | — | — | Me |
| 79 | " | 25 | — | — | Me |
| 80 | (C₁₃—alkyl)—CO—O— | 15 | — | — | Me |
| 81 | " | 10 | — | — | Me |
| 82 | " | 20 | — | — | Me |
| 83 | (C₁₅—alkyl)—CO—O— | 15 | — | — | Me |
| 84 | " | 20 | — | — | Me |
| 85 | (C₉—alkyl)—CO—O— | 10 | — | — | (C₉-alkyl)-CO |
| 86 | " | 15 | — | — | " |
| 87 | " | 20 | — | — | " |
| 88 | (C₁₁—alkyl)—CO—O— | 10 | — | — | (C₁₁-alkyl)-CO |
| 89 | " | 15 | — | — | " |
| 90 | " | 20 | — | — | " |
| 91 | " | 30 | — | — | " |
| 92 | (C₁₂—alkyl)—CO—O— | 10 | — | — | (C₁₂-alkyl)-CO |
| 93 | " | 15 | — | — | " |
| 94 | " | 20 | — | — | " |
| 95 | (C₁₃—alkyl)—CO—O— | 10 | — | — | (C₁₃-alkyl)-CO |
| 96 | " | 20 | — | — | " |
| 97 | (C₁₅—alkyl)—CO—O— | 10 | — | — | (C₁₅-alkyl)-CO |
| 98 | " | 15 | — | — | " |
| 99 | isotridecyl—O— | — | 5 | 10 | H |
| 100 | " | — | 2 | 10 | H |
| 101 | " | 10 | 2 | — | H |
| 102 | " | 10 | 5 | 10 | H |
| 103 (Genamin ® 0 200 Clariant) | C₁₈H₃₅/C₁₆H₃₁—N(—(EO)₁₀H)— | 10 | — | — | H |
| 104 (Atilan ® PTU, Clariant) | C₁₅H₂₉/C₁₇H₃₃—CO—O— | 9 | 2 | — | Me |
| 105 (Genapol ® 3938, Clariant) | C₁₂H₂₅/C₁₄H₂₉—O— | 6 | 4 | — | H |

Preferred as component A) are compounds of the formula (i)

(I)

in which
V is a radical selected from group (V1) to (V4),

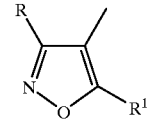

(V1)

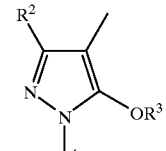

(V2)

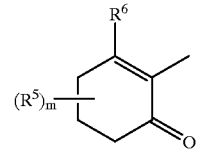

(V3)

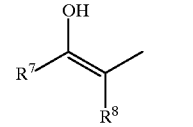

(V4)

where the symbols and indices have the following meanings:
  R is hydrogen, $(C_1-C_{10})$alkoxycarbonyl, $(C_1-C_{10})$haloalkoxycarbonyl, $(C_1-C_{10})$alkylsulfonyl, $(C_1-C_{10})$alkylsulfinyl, $(C_1-C_{10})$alkylthio, COOH or cyano;
  $R^1$ is hydrogen or a $(C_1-C_{10})$ carbon-containing radical such as $(C_1-C_{10})$alkyl, $(C_2-C_{10})$alkenyl, $(C_2-C_{10})$alkynyl, $(C_3-C_{10})$cycloalkyl, $(C_3-C_{10})$cycloalkenyl, ($C_1$–$C_{10}$)alkyl-($C_3$–$C_{10}$)cycloalkyl, ($C_3$–$C_{10}$) halocycloalkyl, ($C_1$–$C_{10}$)alkylthio-cycloalkyl, ($C_1$–$C_{10}$)haloalkyl or ($C_2$–$C_{10}$)haloalkenyl;

$R^2$ is hydrogen, ($C_1$–$C_{10}$)alkyl, ($C_1$–$C_{10}$)alkoxy, ($C_1$–$C_{10}$) haloalkyl, halogen, ($C_1$–$C_{10}$)haloalkoxy, cyano or nitro;

$R^3$ is hydrogen or a ($C_1$–$C_{10}$) carbon-containing radical such as ($C_1$–$C_{10}$)alkyl, ($C_2$–$C_{10}$)alkenyl, ($C_2$–$C_{10}$) alkynyl, ($C_1$–$C_{10}$)haloalkyl, ($C_1$–$C_{10}$)alkoxy-($C_1$–$C_{10}$) alkyl, ($C_1$–$C_{10}$)alkylcarbonyl, ($C_1$–$C_{10}$)alkylsulfonyl, ($C_1$–$C_{10}$)haloalkylsulfonyl, unsubstituted or substituted arylsulfonyl, unsubstituted or substituted arylcarbonyl-($C_1$–$C_{10}$)alkyl or unsubstituted or substituted aryl-($C_1$–$C_{10}$)alkyl;

$R^4$ is hydrogen or a ($C_1$–$C_{10}$) carbon-containing radical such as ($C_1$–$C_{10}$)alkyl, ($C_2$–$C_{10}$)alkenyl, ($C_2$–$C_{10}$) alkynyl, ($C_1$–$C_{10}$)haloalkyl, phenyl or benzyl;

$R^5$ is a ($C_1$–$C_{12}$) carbon-containing radical such as ($C_1$–$C_{10}$)alkyl, ($C_1$–$C_{10}$)alkoxy, ($C_1$–$C_{10}$)alkoxy-($C_1$–$C_{10}$)alkyl, ($C_1$–$C_{10}$)dialkoxy-($C_1$–$C_{10}$)alkyl, ($C_1$–$C_{10}$)alkylthio, halogen, substituted or unsubstituted aryl, tetrahydropyran-4-yl, tetrahydro-pyran-3-yl, tetrahydrothiopyran-3-yl, 1-methylthio-cyclopropyl, 2-ethylthio-propyl, or two radicals $R^5$ together are ($C_2$–$C_{10}$)alkylene;

$R^6$ is hydroxyl or a ($C_1$–$C_{10}$) carbon-containing radical such as ($C_1$–$C_{10}$)alkoxy, ($C_1$–$C_{10}$)haloalkoxy, formyloxy, ($C_1$–$C_{10}$)alkylcarbonyloxy, ($C_1$–$C_{10}$) alkylsulfonyloxy, ($C_1$–$C_{10}$)alkylthio, ($C_1$–$C_{10}$) haloalkylthio, unsubstituted or substituted arylthio, unsubstituted or substituted aryloxy, ($C_1$–$C_{10}$) alkylsulfinyl or ($C_1$–$C_{10}$)alkylsulfonyl;

$R^7$ is a ($C_1$–$C_7$) carbon-containing radical such as ($C_1$–$C_4$) alkyl, ($C_1$–$C_4$) haloalkyl, ($C_3$–$C_7$) cycloalkyl, ($C_1$–$C_4$) alkyl-($C_3$–$C_7$)cycloalkyl, ($C_3$–$C_7$) halocycloalkyl;

$R^8$ is a ($C_1$–$C_4$) carbon-containing radical such as cyano, ($C_1$–$C_4$) alkoxycarbonyl, ($C_1$–$C_4$) alkylcarbonyl, ($C_1$–$C_4$) alkylsulfonyl, ($C_1$–$C_4$) alkylsulfinyl, ($C_1$–$C_4$) alkylthio, ($C_1$–$C_4$) alkylaminocarbonyl, ($C_1$–$C_4$) dialkylaminocarbonyl;

m is an integer from 0 to 6, where, if m≧2, the radicals $R^5$ can be identical or different from one another;

and Z is an unsubstituted or substituted aryl radical, preferably selected from the group (Z1) to (Z5),

(Z1)

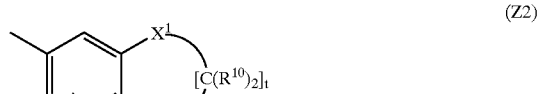
(Z2)

(Z3)

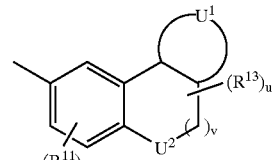
(Z4)

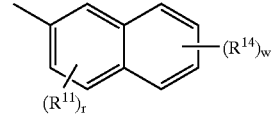
(Z5)

where the symbols and indices have the following meanings:

$R^9$ radicals are identical or different and are nitro, amino, halogen, OH, $SF_5$ or a ($C_1$–$C_{10}$) carbon-containing radical such as ($C_1$–$C_{10}$)alkyl, ($C_2$–$C_{10}$)alkenyl, ($C_2$–$C_{10}$)alkynyl, ($C_1$–$C_{10}$)haloalkyl, ($C_2$–$C_{10}$) haloalkenyl, ($C_2$–$C_{10}$)haloalkynyl, ($C_1$–$C_{10}$) haloalkoxy, ($C_1$–$C_{10}$)haloalkylthio, ($C_1$–$C_{10}$) alkoxycarbonyl, ($C_1$–$C_{10}$)alkylsulfonyl, ($C_1$–$C_{10}$) alkylsulfinyl, ($C_1$–$C_{10}$)alkylthio, arylsulfonyl, arylsulfinyl, arylthio, ($C_1$–$C_{10}$)alkoxy, ($C_1$–$C_{10}$) alkoxy-($C_1$–$C_{10}$)alkoxy, ($C_1$–$C_{10}$)-alkylthio-($C_1$–$C_{10}$)- alkoxy, ($C_1$–$C_{10}$)alkylcarbonyl, ($C_1$–$C_{10}$) alkylaminosulfonyl, ($C_1$–$C_{10}$)dialkylaminosulfonyl, ($C_1$–$C_{10}$)alkylcarbamoyl, ($C_1$–$C_{10}$)dialkylcarbamoyl, ($C_1$–$C_{10}$)alkoxy-($C_1$–$C_{10}$)alkyl, ($C_1$–$C_{10}$)haloalkoxy-($C_1$–$C_{10}$)alkyl, ($C_1$–$C_4$)alkoxy-($C_1$–$C_4$)-alkoxy-($C_1$–$C_4$)-alkoxy-($C_1$–$C_4$)-alkyl, ($C_3$–$C_6$)-cycloalkyl-($C_1$–$C_4$)-alkoxy, ($C_3$–$C_6$)cycloalkoxy-($C_1$–$C_4$)-alkyl, phenoxy, cyano, alkylamino, dialkylamino, unsubstituted or substituted benzyl, unsubstituted or substituted heteroaryl, unsubstituted or substituted heterocyclyl, 2-tetrahydrofuranyl-($C_1$–$C_4$)alkoxy-($C_1$–$C_4$)-alkyl, unsubstituted or substituted heteroaryl-($C_1$–$C_{10}$)alkyl or di-($C_1$–$C_{10}$)alkyl phosphono-($C_1$–$C_{10}$)alkyl;

q is 0, 1, 2, 3, 4 or 5;

$R^{10}$ radicals are identical or different and are hydrogen, ($C_1$–$C_{10}$)alkyl, halogen;

$R^{11}$ radicals are identical or different and are ($C_1$–$C_{10}$) alkyl, ($C_2$–$C_{10}$)alkenyl, ($C_2$–$C_{10}$)alkynyl, halogen, ($C_1$–$C_{10}$)haloalkyl, ($C_2$–$C_{10}$)haloalkenyl, ($C_2$–$C_{10}$) haloalkynyl, ($C_1$–$C_{10}$)haloalkoxy, ($C_1$–$C_{10}$) haloalkylthio, ($C_1$–$C_{10}$)alkoxycarbonyl, ($C_1$–$C_{10}$) alkylsulfonyl, ($C_1$–$C_{10}$)haloalkylsulfonyl, ($C_1$–$C_{10}$) alkylsulfinyl, ($C_1$–$C_{10}$)haloalkylsulfinyl, ($C_1$–$C_{10}$) alkylthio, ($C_1$–$C_{10}$)alkoxy, ($C_1$–$C_{10}$) alkylcarbonyl, ($C_1$–$C_{10}$)alkylaminosulfonyl, ($C_1$–$C_{10}$)dialkylaminosulfonyl, ($C_1$–$C_{10}$)alkylcarbamoyl, ($C_1$–$C_{10}$) dialkylcarbamoyl, ($C_1$–$C_{10}$)alkoxyalkyl, phenoxy, nitro, cyano, aryl or di-($C_1$–$C_{10}$)alkylphosphono-($C_1$–$C_{10}$)alkyl;

$X^1$ is O, $CR^{15}R^{16}$, CHOH, C=O, C=NO($C_1$–$C_{10}$)alkyl;

$X^2$ is O, S, SO, $SO_2$, $CH_2$, NH, N($C_1$–$C_{10}$)alkyl, $NSO_2$ ($C_1$–$C_{10}$)alkyl;

$R^{15}$, $R^{16}$ radicals are identical or different and are hydrogen, ($C_1$–$C_{10}$)alkyl, ($C_1$–$C_{10}$)alkoxy, ($C_1$–$C_{10}$) haloalkoxy, ($C_1$–$C_{10}$)alkylthio, ($C_1$–$C_{10}$)haloalkylthio or $R^{15}$ and $R^{16}$ together form one of the groups —O—$(CH_2)_2$—O—, —O—$(CH_2)_3$—O—, S—$(CH_2)_2$—S—, —S—$(CH_2)_3$—S—, —$(CH_2)_4$—, —$(CH_2)_5$—;

r is 0, 1, 2 or 3;

t is 1 or 2;

$Y^1$, $Y^2$ are $SO_2$ or CO, with the proviso that $Y^1 \neq Y^2$, v is 1 or 2;

$U^1$ together with the carbon atoms to which it is linked forms a carbocyclic or heterocyclic ring which can be aromatic or fully or partially saturated;

$U^2$ is O, S, SO, $SO_2$, $CH_2$, NH, $N(C_1-C_{10})$alkyl, $NSO_2$ $(C_1-C_{10})$alkyl;

$R^{12}$ is hydrogen, $(C_1-C_{10})$alkyl, $(C_3-C_{10})$cycloalkyl, $(C_2-C_{10})$alkenyl, $(C_2-C_{10})$alkynyl, optionally substituted phenyl, optionally substituted benzyl, $(C_1-C_{10})$ acyl;

$R^{13}$ is an unsubstituted or substituted $(C_1-C_{10})$ hydrocarbon radical such as $(C_1-C_{10})$alkyl or aryl;

u is 0, 1 or 2;

$R^{14}$ radicals are identical or different and are nitro, amino, halogen, $SF_5$ or a $(C_1-C_{10})$ carbon-containing radical such as $(C_1-C_{10})$alkyl, $(C_2-C_{10})$alkenyl, $(C_2-C_{10})$ alkynyl, $(C_1-C_{10})$haloalkyl, $(C_2-C_{10})$haloalkenyl, $(C_2-C_{10})$haloalkynyl, $(C_1-C_{10})$haloalkoxy, $(C_1-C_{10})$ haloalkylthio, $(C_1-C_{10})$alkoxycarbonyl, $(C_1-C_{10})$ alkylsulfonyl, $(C_1-C_{10})$alkylsulfinyl, $(C_1-C_{10})$ alkylthio, arylsulfonyl, arylsulfinyl, arylthio, $(C_1-C_{10})$ alkoxy, $(C_1-C_{10})$alkoxy-$(C_1-C_{10})$alkoxy, $(C_1-C_{10})$-alkylthio-$(C_1-C_{10})$-alkoxy, $(C_1-C_{10})$alkylcarbonyl, $(C_1-C_{10})$alkylaminosulfonyl, $(C_1-C_{10})$ dialkylaminosulfonyl, $(C_1-C_{10})$alkylcarbamoyl, $(C_1-C_{10})$dialkylcarbamoyl, $(C_1-C_{10})$alkoxy-$(C_1-C_{10})$ alkyl, $(C_1-C_{10})$haloalkoxy-$(C_1-C_{10})$alkyl, phenoxy, cyano, alkylamino, dialkylamino, unsubstituted or substituted benzyl, unsubstituted or substituted heteroaryl, unsubstituted or substituted heterocyclyl, unsubstituted or substituted heteroaryl-$(C_1-C_{10})$alkyl or di-$(C_1-C_{10})$ alkylphosphono-$(C_1-C_{10})$alkyl, and w is 0,1,2,3 or 4.

A large number of compounds of the formula (I) which are within the scope of the invention can exist in different tautomeric structures, depending on external conditions such as solvent and pH.

Thus, for example, in the event that V=V3 and R6=hydroxyl, several tautomeric structures are possible:

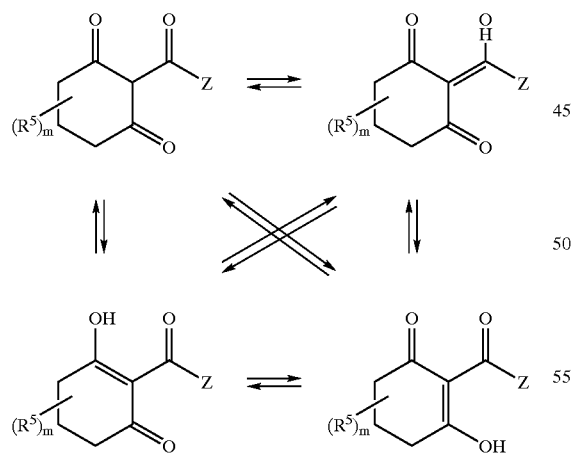

Depending on the nature of the substituents, the compounds of the formula (I) may contain an acidic proton, which can be removed by reaction with a base. Examples of suitable bases are hydrides, hydroxides and carbonates of lithium, sodium, potassium, magnesium and calcium and also ammonia, and organic amines such as triethylamine and pyridine. Such salts are likewise encompassed by the present invention.

Especially preferred are herbicidal compositions according to the invention which comprise compounds of the formula (I)

where

V is a radical (V1), (V3) or (V4),

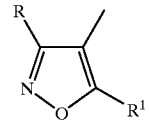

(V1)

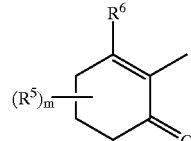

(V3)

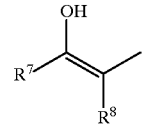

(V4)

where the symbols and indices have the following meanings:

R is hydrogen or $(C_1-C_4)$ alkoxycarbonyl;

$R^1$ is $(C_3-C_8)$cycloalkyl or $(C_1-C_4)$alkyl-$(C_3-C_8)$ cycloalkyl $R^5$ is $(C_1-C_{10})$alkyl, $(C_1-C_4)$ alkoxy or two radicals $R^5$ together are $(C_2-C_6)$alkylene;

$R^6$ is hydroxyl, $(C_1-C_4)$ alkoxy or phenylthio;

$R^7$ is $(C_1-C_4)$ alkyl or $(C_3-C_7)$ cycloalkyl, $R^8$ is $C_1-C_4$ (alkylcarbonyl), $(C_1-C_4)$ alkoxycarbonyl or cyano;

m is 0, 1 or 2;

and Z is a radical (Z1),

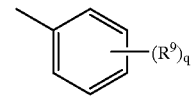

(Z1)

where the symbols and indices have the following meanings:

$R^9$ radicals are identical or different and are nitro, halogen, $(C_1-C_{10})$ haloalkyl, $(C_1-C_{10})$ alkylsulfonyl, $(C_1-C_{10})$haloalkoxy, $(C_1-C_{10})$alkoxy-$(C_1-C_{10})$-alkyl, $(C_1-C_{10})$ haloalkoxy-$(C_1-C_{10})$ alkyl, $(C_1-C_4)$alkoxy-$(C_1-C_4)$-alkoxy-$(C_1-C_4)$-alkoxy-$(C_1-C_4)$-alkyl, $(C_3-C_6)$-cycloalkyl-$(C_1-C_4)$-alkoxy, $(C_3-C_6)$ cycloalkoxy-$(C_1-C_4)$-alkyl, $(C_1-C_{10})$ alkoxy-$(C_1-C_{10})$ alkoxy, 2-tetrahydrofuranyl-$(C_1-C_4)$alkoxy-$(C_1-C_4)$-alkyl, or heterocyclyl, which is unsubstituted or substituted by, for example, one or more radicals selected from the group consisting of halogen, $(C_1-C_{10})$ alkoxy, $(C_1-C_{10})$haloalkoxy, $(C_1-C_{10})$ alkylthio, hydroxyl, amino, nitro, carboxyl, cyano, azido, $(C_1-C_{10})$ alkoxycarbonyl, $(C_1-C_{10})$alkylcarbonyl, formyl, carbamoyl, mono- and di-$(C_1-C_{10})$ alkylaminocarbonyl, acylamino, mono- and di-$(C_1-C_{10})$alkylamino, $(C_1-C_{10})$alkylsulfinyl, $(C_1-C_{10})$ haloalkylsulfinyl, $(C_1-C_{10})$alkylsulfonyl, $(C_1-C_{10})$ haloalkylsulfonyl or unsubstituted or substituted ($C_1$–$C_{10}$)alkyl such as ($C_1$–$C_{10}$)haloalkyl, ($C_1$–$C_{10}$) alkoxyalkyl, ($C_1$–$C_{10}$)haloalkoxyalkyl, ($C_1$–$C_{10}$) alkylthioalkyl, ($C_1$–$C_{10}$)hydroxyalkyl, ($C_1$–$C_{10}$) aminoalkyl, ($C_1$–$C_{10}$)nitroalkyl, ($C_1$–$C_{10}$) carboxyalkyl, ($C_1$–$C_{10}$)cyanoalkyl or ($C_1$–$C_{10}$) azidoalkyl, q is 0, 1, 2, 3, 4 or 5, preferably 2 or 3.

Likewise especially preferred are compositions according to the invention which comprise the compounds of the formula (I) where the symbols and indices have the following meanings:

V is the radical (V 2);
$R^2$ is hydrogen, ($C_1$–$C_4$)-alkyl or ($C_1$–$C_4$)-alkoxy;
$R^3$ is hydrogen or ($C_1$–$C_4$)-alkylsulfonyl;
$R^4$ is methyl, ethyl or n-propyl;
Z is the radical (Z 1);
$R^9$ radicals are identical or different and are nitro, halogen, ($C_1$–$C_4$)haloalkyl or ($C_1$–$C_4$)alkylsulfonyl;
q is 2 or 3.

Very especially preferred are compositions according to the invention which comprise the compounds of the formula (I) where the symbols and indices have the following meanings:

V is a radical (V 1) or (V 3);
R is hydrogen, methoxycarbonyl or ethoxycarbonyl;
$R^1$ is cyclopropyl;
$R^5$ is methyl;
$R^6$ is hydroxyl;
m is 0, 1 or 2;
Z is the radical (Z 1);
$R^9$ radicals are identical or different and are nitro, chlorine, fluorine, bromine, ($C_1$–$C_4$)-haloalkyl, ($C_1$–$C_4$)-alkylsulfonyl, ($C_1$–$C_4$)-haloalkoxy, ($C_1$–$C_4$)-alkoxy-($C_1$–$C_4$)-alkyl, ($C_1$–$C_4$)-haloalkoxy-($C_1$–$C_4$)-alkyl, 2-tetrahydrofuranyl-methoxymethyl, ($C_1$–$C_2$)alkoxy-($C_1$–$C_2$)alkoxy-($C_1$–$C_2$)alkoxy-($C_1$–$C_2$)-alkyl, ($C_3$–$C_6$)-cycloalkoxy-($C_1$–$C_2$)alkyl, ($C_3$–$C_6$)-cycloalkyl-($C_1$–$C_2$)-alkoxy, ($C_1$–$C_4$)-alkoxy-($C_1$–$C_4$)-alkoxy or are 4,5-dihydroisoxazol-3-yl which is substituted by a radical selected from the group consisting of cyanomethyl, ethoxymethyl and methoxymethyl,
q is 2 or 3.

Likewise especially preferred are compositions according to the invention which comprise the compounds of the formula (I) where the symbols and indices have the following meanings:

V is the radical (V 2);
$R^2$ is hydrogen, methyl or ethyl;
$R^3$ is hydrogen, methylsulfonyl or ethylsulfonyl;
$R^4$ is methyl, ethyl or n-propyl;
Z is the radical (Z 1);
$R^9$ radicals are identical or different and are methylsulfonyl, ethylsulfonyl, chlorine, bromine, fluorine, trifluoromethyl, ($C_1$–$C_4$)-alkoxy, ($C_1$–$C_4$)-haloalkoxy or ($C_1$–$C_4$)haloalkoxy-($C_1$–$C_4$)-alkyl;
q is 2 or 3.

Examples of especially preferred compounds of the formula (I) are those mentioned in the following table, and the compound isoxachlortole (A 17).

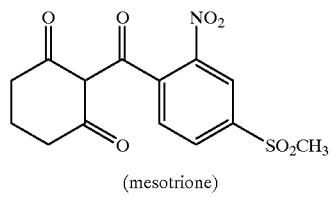
(mesotrione) A1

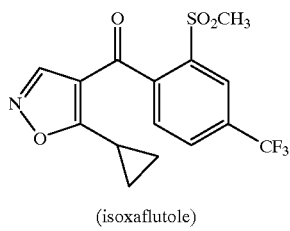
(isoxaflutole) A2

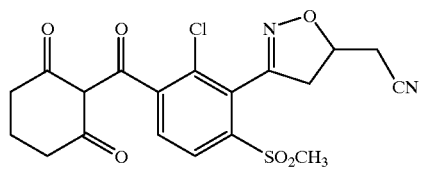
A3

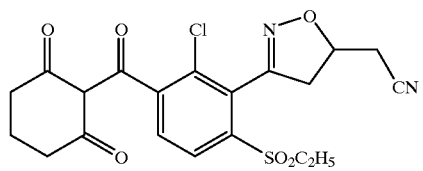
A4

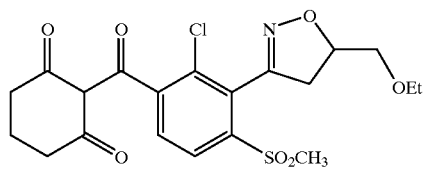
A5

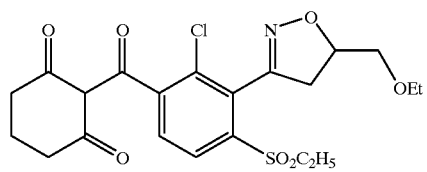
A6

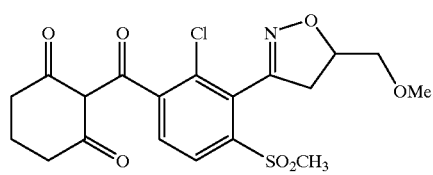
A7

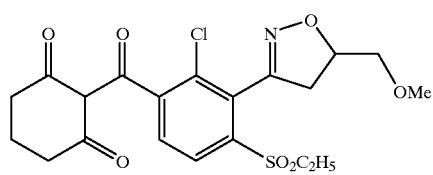
A8

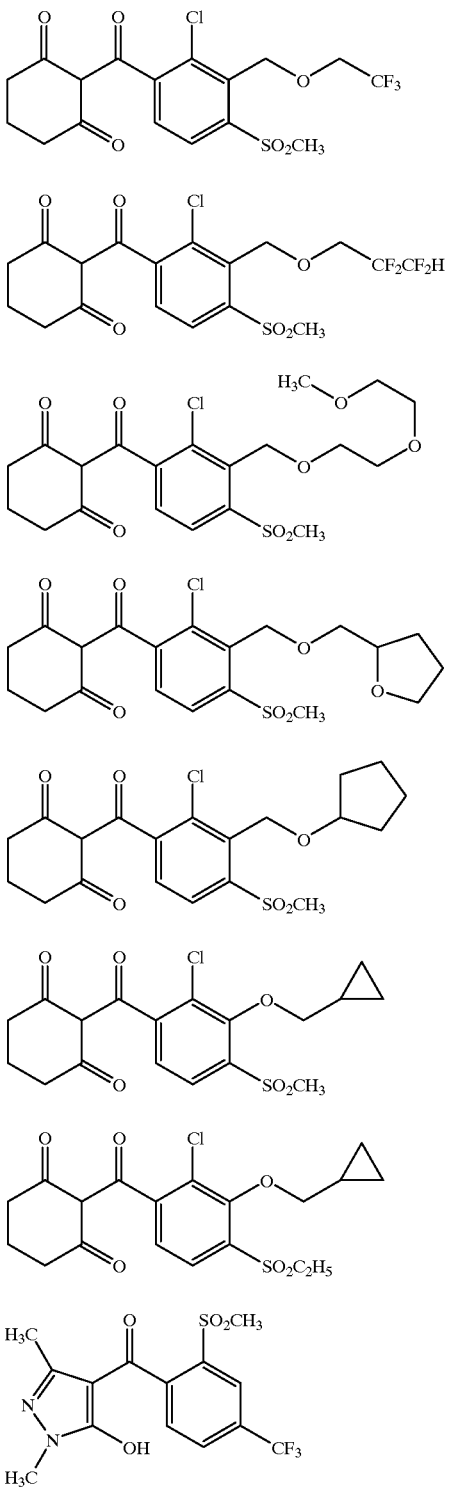

| | |
|---|---|
| A9 | |
| A10 | |
| A11 | |
| A12 | |
| A13 | |
| A14 | |
| A15 | |
| A16 | |

Mixtures of two or more compounds of the formula (I) may also be used as component A).

Unless specifically defined otherwise, the following definitions generally apply to the radicals in the formulae for (I) and (II) and the formulae which follow.

If the term acyl radical is used in the present description, this is to be understood as meaning the radical of an organic acid which originates formally by eliminating an OH group from the organic acid, for example the radical of a carboxylic acid and radicals of acids derived therefrom, such as thiocarboxylic acid, unsubstituted or N-substituted iminocarboxylic acids or the radicals of carbonic monoesters, unsubstituted or N-substituted carbamic acids, sulfonic acids, sulfinic acids, phosphonic acids or phosphinic acids.

An acyl radical is preferably formyl or acyl selected from the group CO—$R^z$, CS—$R^z$, CO—$OR^z$, CS—$OR^z$, CS—$SR^z$, $SOR^z$ or $SO_2R^z$, where $R^z$ denotes in each case a $C_1$–$CO_{10}$ hydrocarbon radical such as $C_1$–$C_{10}$-alkyl or $C_6$–$C_{10}$-aryl which is unsubstituted or substituted, for example by one or more substituents selected from the group consisting of halogen, such as F, Cl, Br, I, alkoxy, haloalkoxy, hydroxy, amino, nitro, cyano or alkylthio, or $R^z$ denotes aminocarbonyl or aminosulfonyl, the two last-mentioned radicals being unsubsituted, N-monosubstituted or N,N-disubstituted, for example by substituents selected from the group consisting of alkyl or aryl. Acyl denotes, for example, formyl, haloalkylcarbonyl, alkylcarbonyl such as ($C_1$–$C_4$)aikylcarbonyl, phenylcarbonyl, it being possible for the phenyl ring to be substituted, or alkyloxycarbonyl, such as ($C_1$–$C_4$) alkyloxycarbonyl, phenyloxycarbonyl, benzyloxycarbonyl, alkylsulfonyl, such as ($C_1$–$C_4$) alkylsulfonyl, alkylsulfinyl, such as $C_1$–$C_4$(alkylsulfinyl), N-alkyl-1-iminoalkyl, such as N-($C_1$–$C_4$)-1-imino-($C_1$–$C_4$) alkyl and other radicals of organic acids.

Carbon-containing radicals are organic radicals containing at least one carbon atom, preferably 1 to 40 carbon atoms, especially preferably 1 to 30 carbon atoms, very especially preferably 1 to 20 carbon atoms, and additionally at least one atom of one or more other elements of the Periodic Table such as H, Si, N, P, O, S, F, Cl, Br or I. Examples of carbon-containing radicals are unsubstituted or substituted hydrocarbon radicals which can be bonded to the skeleton directly or by a hetero atom such as Si, N, S, P or O, unsubstituted or substituted heterocyclyl radicals which can be bonded to the skeleton directly or via a hetero atom such as Si, N, S, P or O, carbon-containing acyl radicals or cyano.

The term hetero atom is to be understood as meaning elements of the Periodic Table which are other than carbon and hydrogen, for example Si, N, S, P, O, F, Cl, Br or I.

Hydrocarbon(oxy) radicals are straight-chain, branched or cyclic unsaturated or saturated aliphatic or aromatic hydrocarbon(-oxy) radicals, for example alkyl, alkenyl, alkynyl or carbocyclic rings such as cycloalkyl, cycloalkenyl or aryl and the hydrocarbonoxy radicals corresponding to these hydrocarbon radicals, such as alkoxy, alkenyloxy, alkynyloxy, cycloalkoxy, cycloalkenyloxy or aryloxy; aryl in this context means a mono-, bi- or polycyclic aromatic system, for example phenyl, naphthyl, tetrahydronaphthyl, indenyl, indanyl, pentalenyl, fluorenyl and the like, preferably phenyl; a hydrocarbon radical preferably denotes alkyl, alkenyl or alkynyl having 1 to 30 carbon atoms or cycloalkyl having 3, 4, 5, 6 or 7 ring atoms or phenyl. Substituted radicals, such as substituted hydrocarbon(-oxy) radicals, for example substituted alkyl, alkenyl, alkynyl or carbocyclic rings such as cycloalkyl, cycloalkenyl or aryl, and the hydrocarbonoxy radicals corresponding to these hydrocarbon radicals, such as alkoxy, alkenyloxy, alkynyloxy, cycloalkoxy, cycloalkenyloxy or phenoxy, or substituted heterocyclyl radicals, denote, for example, a substituted radical derived from the unsubstituted skeleton, where the substituents denote, for example, one or more, preferably 1, 2 or 3, radicals selected from the group consisting of halogen, alkoxy, haloalkoxy, alkylthio, hydroxyl, amino, nitro, carboxy, cyano, azido, alkoxycarbonyl, alkylcarbonyl, formyl, carbamoyl, mono- and dialkylaminocarbonyl, substituted amino, such as acylamino, mono- and dialkylamino, and alkylsulfinyl, haloalkylsulfinyl, alkylsulfonyl, haloalkylsulfonyl and, in the case of cyclic radicals, also unsubstituted or substituted alkyl such as haloalkyl, alkoxyalkyl, haloalkoxyalkyl, alkylthioalkyl, hydroxyalkyl, aminoalkyl, nitroalkyl, carboxyalkyl, cyanoalkyl or azidoalkyl and unsaturated aliphatic radicals which correspond to the abovementioned saturated hydrocarbon-containing radicals, such as alkenyl, alkynyl, alkenyloxy, alkynyloxy and the like. In the case of radicals with carbon atoms, those having from 1 to 4 carbon atoms, in particular 1 or 2 carbon atoms, are preferred. Preferred are, as a rule, substituents selected from the group consisting of halogen, for example fluorine and chlorine, $(C_1-C_4)$alkyl, preferably methyl or ethyl, $(C_1-C_4)$haloalkyl, preferably trifluoromethyl, $(C_1-C_4)$ alkoxy, preferably methoxy or ethoxy, $(C_1-C_4)$haloalkoxy, nitro and cyano. Especially preferred in this context are the substituents methyl, methoxy and chlorine.

The carbon-containing radicals such as alkyl, alkoxy, haloalkyl, haloalkoxy, alkylamino and alkylthio and the corresponding unsaturated and/or substituted radicals can be in each case straight-chain or branched in the carbon skeleton. Unless specified otherwise, the lower carbon skeletons, for example those having 1 to 6 carbon atoms or, in the case of unsaturated groups, those having 2 to 6 carbon atoms, are preferred for these radicals. Alkyl radicals, also in the composite meanings such as alkoxy, haloalkyl and the like, are, for example, methyl, ethyl, n- or i-propyl, n-, 1-, t- or 2-butyl, pentyls, hexyls, such as n-hexyl, 1-hexyl and 1,3-dimethylbutyl, heptyls, such as n-heptyl, 1-methylhexyl and 1,4-dimethylpentyl; alkenyl and alkynyl radicals have the meanings of the unsaturated radicals which are possible and which correspond to the alkyl radicals; for example, alkenyl is allyl, 1-methylprop-2-en-1-yl, 2-methyl-prop-2-en-1-yl, but-2-en-1-yl, but-3-en-1-yl, 1-methyl-but-3-en-1-yl and 1-methyl-but-2-en-1-yl; alkynyl is, for example, propargyl, but-2-yn-1-yl, but-3-yn-1-yl, 1-methyl-but-3-yn-1-yl.

Cycloalkyl is preferably a cyclic alkyl radical having 3 to 8, preferably 3 to 7, especially preferably 3 to 6, carbon atoms, for example cyclopropyl, cyclobutyl, cyclopentyl and cyclohexyl. Cycloalkenyl and cycloalkynyl denote corresponding unsaturated compounds.

Halogen is fluorine, chlorine, bromine or iodine. Haloalkyl, haloalkenyl and haloalkynyl are alkyl, alkenyl or alkynyl, each of which is partially or fully substituted by halogen, preferably by fluorine, chlorine and/or bromine, in particular by fluorine or chlorine, for example $CF_3$, $CHF_2$, $CH_2F$, $CF_3CF_2$, $CH_2FCHCl$, $CCl_3$, $CHCl_2$, $CH_2CH_2Cl$. Haloalkoxy is, for example, $OCF_3$, $OCHF_2$, $OCH_2F$, $CF_3CF_2O$, $OCH_2CF_3$ and $OCH_2CH_2Cl$. The same applies analogously to other halogen-substituted radicals.

A hydrocarbon radical can be an aromatic hydrocarbon radical such as aryl or an aliphatic hydrocarbon radical, an aliphatic hydrocarbon radical generally being a straight-chain or branched saturated or unsaturated hydrocrabon radical, preferably having 1 to 18, especially preferably 1 to 12, carbon atoms, for example alkyl, alkenyl or alkynyl.

Aliphatic hydrocarbon radical preferably means alkyl, alkenyl or alkynyl having up to 12 carbon atoms; the same applies analogously to an aliphatic hydrocarbon radical in a hydrocarbonoxy radical.

A ring denotes a carbocyclic or heterocyclic mono-, bi- or polycyclic unsubstituted or substituted ring system which is saturated, unsaturated or aromatic. Examples of carbocyclic rings are aryl, cycloalkyl or cycloalkenyl.

Aryl is, in general, a mono-, bi- or polycyclic aromatic hydrocarbon radical having preferably 6–20 carbon atoms, with preference 6 to 14 carbon atoms, especially preferably 6 to 10 carbon atoms, which may have fuzed to them mono-, bi- or polycyclic, unsubstituted or substituted aromatic heterocyclyl or mono-, bi- or polycyclic, unsubstituted or substituted saturated or unsaturated carbocyclyl, for example cycloalkyl or cycloalkenyl, or mono-, bi- or polycyclic, unsubstituted or substituted saturated or unsaturated heterocyclyl. Examples of aryl radicals are phenyl, naphthyl, tetrahydronaphthyl, indenyl, indanyl, pentalenyl and fluorenyl, especially preferably phenyl.

Heterocyclic ring, heterocyclic radical or heterocyclyl denotes a mono-, bi- or polycyclic unsubstituted or substituted ring system which is saturated, unsaturated and/or aromatic and contains one or more, preferably 1 to 4, hetero atoms, preferably selected from the group consisting of N, S and O.

Preferred are saturated heterocycles having 3 to 7 ring atoms and one or two hetero atoms selected from the group consisting of N, O and S, the chalcogens not being adjacent. Especially preferred are monocyclic rings having 3 to 7 ring atoms and one hetero atom selected from the group consisting of N, O and S, and also morpholine, dioxolane, piperazine, imidazoline and oxazolidine. Very especially preferred saturated heterocycles are oxirane, pyrrolidone, morpholine and tetrahydrofuran.

Also preferred are partially unsaturated heterocycles having 5 to 7 ring atoms and one or two hetero atoms selected from the group consisting of N, O and S. Especially preferred are partially unsaturated heterocycles having 5 to 6 ring atoms and one hetero atom selected from the group consisting of N, O and S. Very especially preferred partially unsaturated heterocycles are pyrazoline, imidazoline and isoxazoline.

Likewise preferred is heteroaryl, for example mono- or bicyclic aromatic heterocycles having 5 to 6 ring atoms which contain one to four hetero atoms selected from the group consisting of N, O, S, the chalcogens not being adjacent. Especially preferred are monocyclic aromatic heterocycles having 5 to 6 ring atoms which contain one hetero atom selected from the group consisting of N, O and S, and also pyrimidine, pyrazine, pyridazine, oxazole, thiazole, thiadiazole, oxadiazole, pyrazole, triazole and isoxazole. Very especially preferred are pyrazole, thiazole, triazole and furan.

Mono- or disubstituted amino denotes a chemically stable radical selected from the group of the substituted amino radicals, which are N-substituted, for example, by one or two identical or different radicals selected from the group consisting of alkyl, alkoxy, acyl and aryl; preferably monoalkylamino, dialkylamino, acylamino, arylamino, N-alkyl-N-arylamino and N-heterocycles. Preference is given to alkyl radicals having 1 to 4 carbon atoms. Aryl is preferably phenyl. Substituted aryl in this context is preferably substituted phenyl. The definition given further above applies to acyl in this context, preferably $(C_1-C_4)$alkanoyl. This also applies analogously to substituted hydroxylamino or hydrazino.

Optionally substituted phenyl is preferably phenyl which is unsubstituted or mono- or polysubstituted, preferably up to trisubstituted, in the case of halogen such as Cl and F also up to pentasubstituted, by identical or different radicals selected from the group consisting of halogen, $(C_1-C_4)$alkyl, $(C_1-C_4)$alkoxy, $(C_1-C_4)$haloalkyl, $(C_1-C_4)$haloalkoxy and nitro, for example o-, m- and p-tolyl, dimethylphenyls, 2-, 3- and 4-chlorophenyl, 2-, 3- and 4-trifluoro- and -trichlorophenyl, 2,4-, 3,5-, 2,5- and 2,3-dichlorophenyl, o-, m- and p-methoxyphenyl.

Formulae (I) and (II) also encompass all stereo isomers whose atoms are linked topologically in the same manner, and their mixtures. Such compounds contain one or more asymmetric carbon atoms or else double bonds which are not indicated specifically in the general formulae. The stereo isomers which are possible and which are defined by their specific spatial form, such as enantiomers, diastereomers, Z- and E-isomers and tautomers, can be obtained from mixtures of the stereo isomers by customary methods or else be synthesized by stereoselective reactions in combination with the use of stereochemically pure starting materials.

Herbicides of the formula (I) are disclosed, for example, in EP-A 0 137 963, EP-A 0 352 543, EP-A 0 418 175, EP-A 0 496 631, AU-A 672 058, EP-A 0 496 631, WO-A 97/13 765, WO-A 97/01 550, WO-A 97/19 087, WO-A 96/30 368, WO-A 96/31 507, WO-A 96/26 192, WO-A 96/26 206, WO-A 96/10 561, WO-A 96/05 183, WO-A 96/05 198, WO-A 96/05 197, WO-A 96/05 182, WO-A 97/23 491 and WO-A 97/27 187.

The documents cited contain detailed instructions on preparation methods and starting materials. These documents are expressly referred to; they are incorporated into the present description by reference.

The herbicidal compositions according to the invention comprising compounds of the formula (I) and surfactants B) have an outstanding herbicidal action and, in a preferred embodiment, superadditive effects. Owing to the improved control of the harmful plants by the herbicidal compositions according to the invention, it is possible to reduce the application rate and/or to increase the safety margin. Both make sense from an economical and an ecological point of view. The choice of the quantities of components A)+B) to be employed, and the ratio of components A):B), depend on a whole series of factors.

In a preferred embodiment, herbicidal compositions according to the invention comprise a synergistically active content of a combination of the compounds of the formula (I) with surfactants B). In this context, it must be emphasized in particular that even in combinations with application rates or weight ratios of A):B), where synergism cannot be detected easily in each individual case, for example because the individual compounds are usually employed in the combination at very different application rates or else because the control of the harmful plants is already very good, even with the individual compounds, a synergistic effect is generally inherent to the herbicidal compositions according to the invention.

Components A) and B) of the herbicidal compositions according to the invention can be formulated separately and applied by the tank mix method, or else they can be present together in a readymix, which can then be applied in the customary fashion, for example in the form of a spray mixture.

The herbicidal compositions according to the invention can be formulated in various ways, depending on the prevailing biological and/or chemico-physical parameters. Examples of suitable formulations are: wettable powders (WP), water-soluble powders (SP), water-soluble concentrates (SL), emulsifiable concentrates (EC), emulsions (EW) such as oil-in-water and water-in-oil emulsions, sprayable solutions, suspension concentrates (SC), oil- or water-based dispersions, oil-miscible solutions, capsule suspensions (CS), dusts (DP), granules for broadcasting and soil application, granules (GR) in the form of microgranules, spray granules, coated granules and adsorption granules, water-dispersible granules (WG), water-soluble granules (SG), ULV formulations, microcapsules and waxes. These individual types of formulations are known in principle and are described, for example, in Winnacker-Küchler, "Chemische Technologie" [Chemical Engineering], Volume 7, C. Hauser Verlag Munich, 4th Edition. 1986, Wade van Valkenburg, "Pesticide Formulations", Marcel Dekker, N.Y., 1973; K. Martens, "Spray Drying" Handbook, 3rd Ed. 1979, G. Goodwin Ltd. London.

The formulation auxiliaries required, such as inert materials, surfactants, solvents and further additives, are likewise known and are described, for example, in Watkins, "Handbook of Insecticide Dust Diluents and Carriers", 2nd Ed., Darland Books, Caldwell N. J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schonfeldt, "Grenzflächenaktive Äthylenoxidaddukte" [Surface-active ethylene oxide adducts], Wiss. Verlagsgesell., Stuttgart 1976; Winnacker-Küchler, "Chemische Technologie", Volume 7, C. Hauser Verlag Munich, 4th Edition 1986.

Based on these formulations, it is also possible to prepare combinations with other agrochemical active ingredients which differ from component A), such as insecticides, acaricides, herbicides, fungicides, safeners, fertilizers and/or growth regulators, for example in the form of readymix or a tank mix.

Wettable powders are preparations which are uniformly dispersible in water and which, in addition to the active ingredient A) and/or the surfactant B), also contain ionic and/or nonionic surfactants (wetters, dispersants) other than surfactant B), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutyinapthalene-sulfonate or else sodium oleoylmethyltaurate, besides a diluent or inert material. To prepare the wettable powders, the herbicidal active ingredients A) and/or surfactants B) are ground finely, for example in customary apparatuses such as hammer mills, blower mills and air-jet mills, and mixed with the formulation auxiliaries, either simultaneously or in succession.

Emulsifiable concentrates are prepared by dissolving the active ingredient A) and/or the surfactant B) in an organic solvent, for example butanol, cyclohexanone, dimethylformamide, xylene or else higher-boiling aromatics or hydrocarbons or mixtures of the organic solvents with addition of one or more ionic and/or nonionic surfactants (emulsifiers) other than surfactant B). The following are examples of emulsifiers which may be used: calcium alkylarylsulfonates such as calcium dodecylbenzenesulfonate, or nonionic emulsifiers such as fatty acid polyglycol esters, alkylaryl polyglycol ethers, fatty alcohol polyglycol ethers, propylene oxide/ethylene oxide condensates, alkyl polyethers, sorbitan esters such as, for example, sorbitan fatty acid esters or polyoxyethylene sorbitan esters such as, for example, polyoxyethylene sorbitan fatty acid esters.

Water-soluble concentrates are obtained for example by dissolving the active ingredient A) and/or the surfactant B) in water or in a water-miscible solvent and, if appropriate, adding further additives such as water-soluble surfactants to the solution.

Dusts are obtained by grinding the active ingredient A) and/or the surfactant B) with finely divided solid materials, for example talc, natural clays such as kaolin, bentonite and pyrophyllite, or diatomaceous earth.

Suspension concentrates may be water- or oil-based. They can be prepared for example by wet-grinding by means of commercially available bead mills with or without addition of surfactants other than surfactant B), as they have already been mentioned, for example above in the case of the other formulation types.

Emulsions, for example oil-in-water emulsions (EW), can be prepared for example by means of stirrers, colloid mills and/or static mixers using aqueous organic solvents and, if appropriate, surfactants other than surfactant B), as they have already been mentioned, for example above in the case of the other formulation types.

Granules can be prepared either by spraying the active ingredient A) and/or surfactant B) onto adsorptive granulated inert material or by applying active ingredient concentrates to the surface of carriers such as sand, kaolinites or granulated inert material with the aid of stickers, for example polyvinyl alcohol, sodium polyacrylate or else mineral oils. Suitable active ingredients A) and/or surfactants B) may also be granulated in the fashion which is conventional for the production of fertilizer granules, if desired as a mixture with fertilizers.

Water-dispersible granules are generally prepared by the customary methods such as spray drying, fluid-bed granulation, disc granulation, mixing with high-speed stirrers and extrusion without a solid inert material.

To prepare disc granules, fluidized-bed granules, extruder granules and spray granules, see, for example, methods in "Spray-Drying Handbook" 3rd ed. 1979, G. Goodwin Ltd., London; J. E. Browning, "Agglomeration", Chemical and Engineering 1967, pages 147 et seq.; "Perry's Chemical Engineer's Handbook", 5th Ed., McGraw-Hill, New York 1973, pp. 8–57.

For further details on the formulation of crop protection products, see, for example, G. C. Klingman, "Weed Control as a Science", John Wiley and Sons, Inc., New York, 1961, pages 81–96 and J. D. Freyer, S. A. Evans, "Weed Control Handbook", 5th Ed., Blackwell Scientific Publications, Oxford, 1968, pages 101–103.

As a rule, the herbicidal compositions according to the invention comprise 0.01 to 99% by weight, in particular 0.1 to 95% by weight, of one or more compounds of the formula (I).

In wettable powders, the active ingredient concentration is, for example, approximately 10 to 90% by weight, the remainder to 100% being composed of customary formulation constituents and, if appropriate, surfactants B). In the case of emulsifiable concentrates, the active ingredient concentration can amount to approximately 1 to 90, preferably 5 to 80, % by weight. Formulations in the form of dusts comprise 1 to 30% by weight of active ingredient, in most cases 5 to 20% by weight of active ingredient, and sprayable solutions comprise approximately 0.05 to 80, preferably 2 to 50, % by weight of active ingredient. In the case of water-dispersable granules, the active ingredient content depends partly on whether the active compound is present in liquid or solid form and on the granulation auxiliaries, fillers and the like which are being used. In the case of the water-dispersible granules, for example, the active ingredient content is between 1 and 95% by weight, preferably between 10 and 80% by weight.

In addition, the active ingredient formulations mentioned comprise, if appropriate, the auxiliaries which are conventional in each case, such as adhesives, wetters, dispersants, emulsifiers, penetrants, preservatives, antifreeze agents, solvents, fillers, carriers, colorants, antifoams, adjuvants such as mineral oils or vegetable oils and their derivatives, evaporation inhibitors, and pH and viscosity regulators.

The herbicidal compositions according to the invention can be prepared by customary methods, for example by mixing the components with the aid of stirrers, shakers or (static) mixers.

A preferred embodiment of the present invention consists in mixing the formulations which comprise the compounds of the formula (I) with surfactants B) and/or their formulations in the spray tank. To this end, the compounds of the formula (I) can be formulated as water-dispersible granules, for example on a kaolin basis, where the content of compounds of the formula (I) can vary within wide ranges between 0.01 and 99% by weight, preferably between 0.5 and 80% by weight. In addition to the compounds of the formula (I), these formulations may comprise further agrochemical active ingredients, such as safeners, for example in an amount of 0.1–50% by weight, preferably 0.5–40% by weight. The surfactants B) can be added as such or in formulated form, preferably as a liquid product such as water-soluble concentrates or emulsifiable concentrates.

The readymixes can be obtained by preparing for example emulsifiable concentrates or oil dispersions from compounds of the formula (I), surfactants B) and further auxiliaries. In the readymixes, the content of compounds of the formula (I) can vary within wide limits; in general, it is between 0.01 and 99%, preferably between 0.1 and 60% by weight. The content of surfactants B) can also vary within wide limits; it is generally between 1 and 80% by weight, as a rule between 5 and 50% by weight. Finally, the readymixes may also comprise further agrochemical active ingredients, such as safeners, for example in an amount of 0.01–60% by weight, preferably 0.1–40% by weight.

If appropriate, the formulations may comprise auxiliaries such as solvents, for example aromatic solvents such as xylenes or mixtures of aromatics from the Solvesso® series, such as Solvesso® 100, Solvesso® 150 or Solvesso® 200 by Exxon; aliphatic or isoparaffinic solvents such as products from the Exxol®-D or Isopur® series by Exxon, oils of vegetable or animal origin and their derivatives, such as rapeseed oils or rapeseed oil methyl esters; esters such as butyl acetate; ethers such as diethyl ether, THF or dioxane. The solvent content is preferably 1–95% by weight, especially preferably 5–80% by weight. Examples of further suitable auxiliaries are emulsifiers (preferred content: 0.1–10% by weight), dispersants (preferred content: 0.1–10% by weight) and thickeners (preferred content: 0.1–5% by weight), and, if appropriate, stabilizers such as antifoams, water binders, acid binders and crystallization inhibitors.

The herbicidal compositions according to the invention can be employed pre- or post-emergence, for example by spraying. By employing the mixtures, the product quantity required for effecting weed control can be reduced substantially.

As a rule, the surfactants B) to be used in accordance with the invention are applied together with the compound(s) A) or immediately in succession, preferably in the form of a spray mixture which comprises the surfactants B) and the compounds A) in effective amounts and, if appropriate, further customary auxiliaries. The spray mixture is preferably prepared on the basis of water and/or an oil, for example a high-boiling hydrocarbon such as kerosene or paraffin. The herbicidal compositions according to the invention may be formulated as the tank mix or a "ready-mix".

The weight ratio of compounds A) to surfactant B) can vary within a wide range and depends, for example, on the efficacy of the herbicide. As a rule, it is in the range of from 10:1 to 1:5000, preferably from 4:1 to 1:2000.

In general, the application rates of the compound(s) of the formula (I) are between 0.1 and 500 g A.S./ha (A.S.=active substance, i.e. application rate based on the active compound), preferably between 0.5 and 200 g of a.i./ha. The application rates of surfactants B) are generally between 1 and 5000 g surfactant/ha, with between 10 and 2000 g surfactant/ha being preferred.

The concentration of the surfactants B) to be used in accordance with the invention is, in a spray mixture, generally from 0.05 to 4% by weight, preferably 0.1 to 1% by weight, in particular 0.1 to 0.3% by weight, of surfactant.

The herbicidal compositions according to the invention have an excellent herbicidal activity against a broad range of economically important monocotyledonous and dicotyledonous harmful plants. The active substances also act efficiently on perennial weeds which produce shoots from rhizomes, rootstocks or other perennial organs and which are difficult to control. In this context, it does not matter whether the substances are applied before sowing, pre-emergence or post-emergence. Specifically, examples may be mentioned of some representatives of the monocotyledonous and dicotyledonous weed flora which can be controlled by the compositions according to the invention, without the enumeration being a restriction to certain species.

Examples of weed species on which the active substance acts efficiently are, from amongst the monocotyledons, Avena, Lolium, Alopecurus, Phalaris, Echinochloa, Digitaria, Setaria and also Cyperus species from the annual sector and from amongst the perennial species Agropyron, Cynodon, Imperata and Sorghum, and also perennial Cyperus species.

In the case of the dicotyledonous weed species, the range of action extends to species such as, for example, Galium, Viola, Veronica, Lamium, Stellaria, Amaranthus, Sinapis, Ipomoea, Matricaria, Abutilon and Sida from amongst the annuals, and Convolvulus, Cirsium, Rumex and Artemisia in the case of the perennial weeds.

The compositions according to the invention likewise effect outstanding control of weeds which occur under the specific conditions of rice growing, such as, for example, Echinochloa, Sagittaria, Alisma, Eleocharis, Scirpus and Cyperus.

If the compositions according to the invention are applied to the soil surface before germination, then the weed seedlings are either prevented completely from emerging, or the weeds grow until they have reached the cotyledon stage but then their growth stops, and, eventually, after three to four weeks have elapsed, they die completely.

If the compositions are applied post-emergence to the green parts of the plants, growth likewise stops drastically a very short time after the treatment and the weed plants remain at the growth stage of the point of time of application, or they die completely after a certain time, so that in this manner competition by the weeds, which is harmful to the crop plants, is eliminated at a very early point in time and in a sustained manner.

Even though the compositions according to the invention have an excellent herbicidal activity against monocotyledonous and dicotyledonous weeds, crop plants of economically important crops, such as dicotyledonous crops, like soya, cotton, oilseed rape, sugarbeet, in particular soya, or Gramineae crops like wheat, barley, rye, rice or maize are damaged not at all, or only to a negligible extent. For these reasons, the present compounds are highly suitable for selectively controlling undesired plant growth in plantings for agricultural or ornamental use.

In addition, the herbicidal compositions according to the invention have excellent growth-regulatory properties in crop plants. They engage in the plant metabolism in a regulatory fashion and can thus be employed for the targetted control of plant constitutents and for facilitating harvesting, such as, for example, by provoking desiccation and stunted growth. Furthermore, they are also suitable for generally regulating and inhibiting undesired vegetative growth, without simultaneously destroying the plants. Inhibition of vegetative growth plays an important role in many monocotyledonous and dicotyledonous crops because lodging can be reduced hereby, or prevented completely.

Owing to their herbicidal and plant-growth-regulatory properties, the herbicidal compositions according to the invention can also be employed for controlling harmful plants in crops of genetically modified plants which are known or are yet to be developed. As a rule transgenic plants are distinguished by particular advantageous properties, for example by resistances to certain pesticides, in particular certain herbicides, resistances to plant diseases or pathogens of plant diseases, such as certain insects or microorganisms such as fungi, bacteria or viruses. Other special properties relate to, for example, the harvested material with regard to quantity, quality, shelf life, composition and specific constituents. Thus, transgenic plants are known which have an increased starch content or a modified starch quality, or others which have a different fatty acid composition of the harvested material.

The use of the compositions according to the invention in economically important transgenic crops of useful plants and ornamentals, for example cereals such as wheat, barley, rye, oats, sorghum and millet, rice, cassava and maize, or else crops of sugar beet, cotton, soya, oilseed rape, potato, tomato, pea and other vegetables, is preferred. The compositions according to the invention can preferably be employed as herbicides in crops of useful plants which are resistant, or have been made resistant by genetic engineering, to the phytotoxic effects of the herbicides.

When using the herbicidal compositions according to the invention in transgenic crops, effects are frequently observed in addition to the effects against harmful plants to be observed in other crops, which are specific for application in the transgenic crop in question, for example a modified or specifically widened wheat spectrum which can be controlled, modified application rates which may be employed for application, preferably good combining ability with the herbicides to which the transgenic crop is resistant, and an effect on growth and yield of the transgenic crop plants.

The subject matter of the invention is thus also the use of the compositions according to the invention as herbicides for controlling harmful plants, preferably in plant crops, it also being possible for the plant crops to be transgenic plant crops.

The herbicidal compositions according to the invention can also be employed nonselectively for controlling undesired vegetation, for example on verges, squares, industrial terrain and railway installations.

Owing to the relatively low application rate of the herbicidal compositions according to the invention, they are, in general, already very well tolerated. In particular, a reduction in the absolute application rate is achieved with the combinations according to the invention, compared with the individual use of a herbicidal active ingredient.

If it is desired to increase the tolerance and/or selectivity of the herbicidal compositions according to the invention even further, it may be advantageous to apply them jointly in a mixture or staggered in time in succession together with safeners or antidotes.

Examples of compounds which are suitable as safeners or antidotes for the herbicidal compositions according to the invention are known, for example, from EP-A-333 131 (ZA-89/1960), EP-A-269 806 (U.S. Pat. No. 4,891,057), EP-A-346 620 (AU-A-89/34951) and the international patent applications PCT/EP 90/01966 (WO-91108202) and PCT/EP 90102020 (WO-911078474) and the literature cited therein or can be prepared by the processes described therein. Other suitable safeners are known from EP-A-94 349 (U.S. Pat. No. 4,902,304), EP-A-191 736 (U.S. Pat. No. 4,881,966) and EP-A-0 492 366 and the literature cited therein.

In a preferred embodiment, the herbicidal compositions of the present invention therefore comprise an additional content of C) one or more compounds which act as safeners or antidotes.

Preferred antidotes or safeners or groups of compounds which are suitable as safeners or antidotes in the herbicidal compositions according to the invention are, inter alia:

a) compounds of the dichlorophenylpyrazolyl-3-carboxylic acid type, preferably compounds such as methyl 1-(2,4-dichlorophenyl)-5-(ethoxycarbonyl)-5-methyl-2-pyrazoline-3-carboxylate (mefenpyr-diethyl, compound C1-1) and related compounds as they are described in the international application WO 91/07874 (PCT/EP 90102020);

b) dichlorophenylpyrazolecarboxylic acid derivatives, preferably compounds such as ethyl 1-(2,4-dichlorophenyl)-5-methyl-pyrazole-3-carboxylate (compound C1-2), ethyl 1-(2,4-dichlorophenyl)-5-isopropyl-pyrazole-3-carboxylate (compound C1-3), ethyl 1-(2,4-dichlorophenyl)-5-(1,1-di-methyl-ethyl) pyrazole-3-carboxylate (compound C1-4), ethyl 1-(2,4-dichlorophenyl)-5-phenyl pyrazole-3-carboxylate (compound C1-5) and related compounds as they are described in EP-A-0 333 131 and EP-A-0 269 806;

c) compounds of the triazolecarboxylic acid type, preferably compounds such as ethyl 1-(2,4-dichlorophenyl)-5-trichloromethyl-(1H)-1,2,4-triazole-3-carboxylate (compound C1-6, fenchlorozole-ethyl) and related compounds (see EP-A-0 174 562 and EP-A-0 346 620);

d) compounds of the dichlorobenzyl-2-isoxazoline-3-carboxylic acid type, compounds of the 5-benzyl- or 5-phenyl-2-isoxazoline-3-carboxylic acid type, preferably compounds such as ethyl 5-(2,4-dichlorobenzyl)-2-isoxazoline-3-carboxylate (compound C1-7) or ethyl 5-phenyl-2-isoxazoline-3-carboxylate (compound C1-8) and related compounds as they are described in International Patent Application WO 91/08202 (PCT/EP 90101966);

e) compounds of the 8-quinolinoxyacetic acid type, preferably compounds such as 1-methyl-hex-1-yl (5-chloro-8-quinolinoxy) acetate (cloquintocet-mexyl, C2-1), 1,3-dimethylbut-1-yl (5-chloro-8-quinolinoxy) acetate (C2-2), 4-allyl-oxybutyl (5-chloro-8-quinolinoxy) acetate (C2-3), 1-allyl-oxy-prop-2-yl (5-chloro-8-quinolinoxy) acetate (C2-4), ethyl (5-chloro-8-quinolinoxy) acetate (C2-5), methyl (5-chloro-8-quinolinoxy) acetate (C2-6), allyl (5-chloro-8-quinolinoxy) acetate (C2-7), 2-(2-propylidene-iminoxy)-1-ethyl (5-chloro-8-quinolinoxy) acetate (C2-8), 2-oxoprop-1-yl (5-chloro-8-quinolinoxy) acetate (C2-9) and related compounds as they are described in EP-A-0 086 750, EP-A-0 094 349 and EP-A-0 191 736 or EP-A-0 492 366;

f) compounds of the (5-chloro-8-quinolinoxy) malonic acid type, preferably compounds such as diethyl (5-chloro-8-quinolinoxy) malonate, diallyl (5-chloro-8-quinolinoxy) malonate, methyl ethyl (5-chloro-8-quinolinoxy) malonate and related compounds as they have been described and proposed in German Patent Application EP-A-0 582 198;

g) active ingredients of the type of the phenoxyacetic- or -propionic acid derivatives or of the aromatic carboxylic acids such as, for example, 2,4-dichlorophenoxyacetic acid ester (2,4-D), 4-chloro-2-methylphenoxypropionic acid ester (mecoprop), MCPA or 3,6-dichloro-2-methoxybenzoic acid (and its ester) (dicamba);

h) compounds of the 5,5-diphenyl-2-isoxazoline-3-carboxylic acid type, preferably ethyl 5,5-diphenyl-2-isoxazoline-3-carboxylate (isoxadifen-ethyl, C3-1);

i) compounds which are known as safeners for, for example, rice such as fenclorim (=4,6-dichloro-2-phenylpyrimidine, Pesticide Manual, 11th Edition, 1997, pp. 511–512), dimepiperate (=S-1-methyl-1-phenylethyl piperidine-1-thiocarboxylate, Pesticide Manual, 11th Edition, 1997, pp. 404–405), daimuron (=1-(1-methyl-1-phenylethyl)-3-p-tolylurea, Pesticide Manual, 11th Edition, 1997, p. 330), cumyluron (=3-(2-chlorophenylmethyl)-1-(1-methyl-1-phenyl-ethyl)-urea, JP-A-60/087254), methoxyphenone (=3,3'-dimethyl-4-methoxy-benzophenone, CSB (=1-bromo-4-(chloromethylsulfonyl) benzene, CAS Reg. No. 54091-06-4).

Moreover, at least some of the abovementioned compounds are described in EP-A-0 640 587, which is herewith referred to for disclosure purposes.

j) A further important group of compounds which are suitable as safeners and antidotes is disclosed in WO 95107897.

The safeners (antidotes) of the above groups a) to j) reduce or suppress phytotoxic effects which may occur when using the herbicidal compositions according to the invention in crops of useful plants, without adversely affecting the efficacy of the herbicides against harmful plants. Thus, the field of application of the herbicidal compositions according to the invention can be widened substantially, and, in particular, the use of safeners makes possible the use of combinations which could previously only be employed with limited or insufficient success, i.e. combinations which, when applied without safener and in low dosages with a narrow spectrum of action, lead to insufficient control of the harmful plants.

The herbicidal compositions according to the invention and the abovementioend safeners can be applied together (as a readymix or by the tank mix method) or in succession in any desired sequence. The weight ratio of safener:herbicide (compound(s) of the formula (I)) can vary within wide limits and is preferably in the range of from 1:100 to 100:1, in particular of from 1:10 to 10:1. The amounts of herbicide(s) and safener(s) which are optimal in each case usually depend on the type of the herbicidal composition and/or on the safener used and on the species of the plant stand to be treated.

Depending on their properties, the safeners of type C) can be used for pretreating the seed of the crop plant (seed treatment) or introduced into the seed furrows prior to sowing or applied together with the herbicide mixture before or after emergence of the plants.

Pre-emergence treatment includes not only the treatment of the area under cultivation prior to sowing, but also the treatment of areas under cultivation where the crop has been sown, but has not emerged yet. Preferred is the concommitant use with the herbicide mixture. To this end, tank mixes or readymixes may be employed.

Depending on the indication of the herbicide used, the application rates of the safeners required can vary within wide limits and are, as a rule, in the range of from 0.001 to 1 kg, preferably from 0.005 to 0.2 kg, of active ingredient per hectare. Subject matter of the present invention is also a method of controlling undesired plants, preferably in plant crops, which comprises applying a herbicidally effective amount of the herbicidal composition according to the invention to the plants, plant parts, seeds of the plants, or the area under cultivation.

A preferred variant of the method is to apply the herbicidal compositions according to the invention in the form of tank mixes, where the individual components (for example in the form of formulations) are mixed together in the tank with water or an oil, and the resulting spray mixture is applied. Since the crop plant tolerance of the combinations according to the invention is excellent while simultaneously effecting very good control of the harmful plants, the combinations can be regarded as selective. In a preferred modification of this method, herbicidal compositions are therefore employed for the selective control of undesired plants.

The herbicidal compositions can be applied in the customary fashion, for example with water and/or oil as carrier, at spray mixture rates of approximately 0.5–4000, preferably 100 to 1000, liters/ha. An application of the compositions by the low-volume and ultra-low volume methods (ULV) is also possible, as is their application in the form of granules and microgranules.

A preferred use relates to the application of herbicidal compositions, which exhibit contents of components A) and B) in a synergistically active amount. The invention also includes mixtures of one or more components A), preferably A1, A2, A3 and/or A4, and one or more component B), if appropriate in combination with one or more safeners C).

As preferred examples for the herbicidal compositions according to the invention, the following combinations of A1, A2, A3 and/or A4 with surfactants B) may be mentioned, without this constituting a limitation to combinations which have been mentioned explicitly:

A1 in combination with one of the surfactants of group B1 to B105 (see Table 1)

A2 in combination with one of the surfactants of the group B1 to B105 (see Table 1)

A3 in combination with one of the surfactants of the group B1 to B105 (see Table 1)

A4 in combination with one of the surfactants of the group B1 to B105 (see Table 1)

A5 in combination with one of the surfactants of the group B1 to B105 (see Table 1)

A6 in combination with one of the surfactants of the group B1 to B105 (see Table 1)

A7 in combination with one of the surfactants of the group B1 to B105 (see Table 1)

A8 in combination with one of the surfactants of the group B1 to B105 (see Table 1)

A9 in combination with one of the surfactants of the group B1 to B105 (see Table 1)

A10 in combination with one of the surfactants of the group B1 to B105 (see Table 1)

A11 in combination with one of the surfactants of the group B1 to B105 (see Table 1)

A12 in combination with one of the surfactants of the group B1 to B105 (see Table 1)

A13 in combination with one of the surfactants of the group B1 to B105 (see Table 1)

A14 in combination with one of the surfactants of the group B1 to B105 (see Table 1)

A15 in combination with one of the surfactants of the group B1 to B105 (see Table 1)

A16 in combination with one of the surfactants of the group B1 to B105 (see Table 1)

A17 in combination with one of the surfactants of the group B1 to B105 (see Table 1)

The use of a safener may be advantageous in the abovementioned combinations since this makes it possible to reduce potential damage to the crop plant which may be caused by herbicides A) or other herbicidally active ingredients.

In addition, and to complement the characteristics, the herbicidal compositions of the present invention may additionally comprise one, two or more agrochemical active ingredients (for example, herbicides, insecticides or fungicides) other than component A), in general in minor quantities.

This leads to a large number of possibilities of combining several active ingredients with each other and of employing them jointly for controlling harmful plants, preferably in plant crops, without deviating from the inventive concept.

In conclusion, it can be said that the joint application of compounds of the formula (I) with one or more surfactants B) results in an outstanding herbicidal action. In a preferred embodiment, the action of the herbicidal compositions according to the invention exceeds the action of the individual components employed when used singly.

These effects permit, inter alia, a reduced application rate, the control of a broader spectrum of dicotyledonous and monocotyledonous weeds, the closure of control gaps, also with regard to resistant species, more rapid and safer action, complete control of the harmful plants with only one or few applications, and a widened period of use.

The abovementioned characteristics are required in weed control practice in order to keep agricultural crops free from undesired competing plants and thus guaranteeing and/or increasing the yields in terms of quality and quantity. The state of the art is exceeded markedly by the combinations according to the invention with regard to the above-described properties. Moreover, the combinations according to the invention allow in the most outstanding fashion the control of otherwise resistant harmful plants.

EXAMPLES

Seeds or rhizome pieces of monocotyledonous and dicotyledonous weed plants were placed in sandy loamy soil in plastic pots, covered with soil and grown in the greenhouse under favorable growth conditions. Three weeks after sowing, the test plants were treated in the three-leaf stage. The compounds according to the invention which were formulated in the form of wettable powders or emulsion concentrates were sprayed onto the green plant parts at an application rate of 600 to 800 l of water/ha (converted), in various dosages. After the test plants had been left to stand in the greenhouse under optimum growth conditions for 3 to 4 weeks the effect of the preparations was scored visually by comparison with untreated controls. The compositions according to the invention exhibit a good herbicidal activity against economically important harmful plants.

For example, the action of herbicide A1 (application rate 200 g/ha) and of herbicides A4, A6 and A9 (application rates in each case 80 g/ha) is increased markedly by combining them with a surfactant such as Genapol X 150, Genapol X 200, Sapogenat T130, Sapogenat T 200, Sapogenat T 300, Sapogenat T 400, Sapogenat T 500 or Genapol O 200 at application rates of, for example, 50 g/ha, 100 g/ha, 300 g/ha and 500 g/ha in comparison with, for example, the application of the abovementioned herbicides without surfactant or with a surfactant with a low ethylene oxide unit content such as Genapol O 060 or Sapogenat T 040 (6 and 4 ethylene oxide units, respectively).

The comparative examples mentioned in the table hereinbelow demonstrate the particularly high herbicidal action of the compositions according to the invention (Nos 4, 5 and 6) in comparison with the action of the herbicide without surfactant (No. 1) or in comparison with the action of the herbicide together with surfactants with a low ethylene oxide unit content (Nos 2 and 3).

The herbicides were formulated in each case as wettable powders with an active ingredient content of 20%.

|   | Herbicide | Surfactant | Herbicidal action against | |
|---|---|---|---|---|
| No. | (80 g/ha) | (300 g/ha) | Monocots | Dicots |
| 1 | A4 | — | 3% | 29% |
| 2 | A4 | Genapol O 080 | 12% | 55% |
| 3 | A4 | Sapogenat T 040 | 12% | 44% |
| 4 | A4 | Genapol O 200 | 38% | 61% |
| 5 | A4 | Sapogenat T 300 | 40% | 57% |
| 6 | A4 | Sapogenat T 500 | 49% | 72% |

We claim:

1. The herbicidal composition comprising

A) a compound of the formula

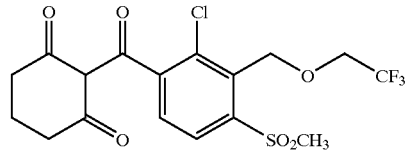

and, B) a surfactant to mixture has the formula

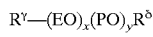

wherein $R^\gamma$ is $C_{12}H_{25}$ or $C_{14}H_{29}$—O—

X is 56

Y is 4

$R^\delta$ is H.

* * * * *

UNITED STATES PATENT AND TRADEMARK OFFICE
CERTIFICATE OF CORRECTION

PATENT NO. : 6,835,695 B2
APPLICATION NO. : 09/882395
DATED : December 28, 2004
INVENTOR(S) : Krause et al.

It is certified that error appears in the above-identified patent and that said Letters Patent is hereby corrected as shown below:

1) Claim 1, Column 28, line 26, the definition of substituent X should read "X is 6" instead of "X is 56".

Signed and Sealed this

Eleventh Day of July, 2006

JON W. DUDAS
*Director of the United States Patent and Trademark Office*